(12) United States Patent
Argenbright et al.

(10) Patent No.: US 8,396,720 B2
(45) Date of Patent: Mar. 12, 2013

(54) PATIENT DIAGNOSIS USING TRIAGE PROTOCOLS THAT HAVE CUSTOMIZED MESSAGES AT EXIT POINTS

(75) Inventors: Keith E. Argenbright, Fort Worth, TX (US); Ronald E. Galbraith, Nashville, TN (US); Audrey J. Nudd, Round Rock, TX (US)

(73) Assignee: Numoda Technologies, Inc., Philadelphia, PA (US)

( * ) Notice: Subject to any disclaimer, the term of this patent is extended or adjusted under 35 U.S.C. 154(b) by 2062 days.

(21) Appl. No.: 10/240,479

(22) PCT Filed: Apr. 5, 2001

(86) PCT No.: PCT/US01/11000
§ 371 (c)(1),
(2), (4) Date: Oct. 2, 2002

(87) PCT Pub. No.: WO01/77949
PCT Pub. Date: Oct. 18, 2001

(65) Prior Publication Data
US 2003/0208377 A1      Nov. 6, 2003

Related U.S. Application Data

(60) Provisional application No. 60/195,001, filed on Apr. 5, 2000.

(51) Int. Cl.
*G06Q 10/00*   (2006.01)
*G06F 9/44*    (2006.01)
(52) U.S. Cl. .......................................... 705/2; 717/106
(58) Field of Classification Search .................. 705/2–4; 707/3
See application file for complete search history.

(56) References Cited

U.S. PATENT DOCUMENTS

| | | | |
|---|---|---|---|
| 5,594,638 A | | 1/1997 | Iliff |
| 5,786,816 A | * | 7/1998 | Macrae et al. ................. 715/837 |
| 5,911,145 A | * | 6/1999 | Arora et al. .................... 715/207 |
| 6,037,940 A | | 3/2000 | Schroeder et al. |
| 6,139,494 A | | 10/2000 | Cairnes |
| 6,206,829 B1 | | 3/2001 | Iliff |
| 6,234,964 B1 | * | 5/2001 | Iliff ............................. 600/300 |
| 6,656,114 B1 | * | 12/2003 | Poulsen et al. ................. 600/300 |

OTHER PUBLICATIONS

Guterman et al., Assessing the effectiveness of a computer-based decision support system for emergency department triage, 1993, IEEE.*

(Continued)

*Primary Examiner* — Robert Morgan
*Assistant Examiner* — Rachel L Porter
(74) *Attorney, Agent, or Firm* — Panitch Schwarze Belisario & Nadel LLP

(57) ABSTRACT

A decison flowchart of a triage protocol is provided for a medical condition of a patient. The flowchart includes a plurality of decision blocks. Each decision block relates to one or more patient symptoms and/or considerations. A plurality of exit points are provided in the flowchart. Each exit point is associated with a respective decision block. Each exit point is reached upon the presence or absence of a symptom or consideration in the respective decision block. Each exit point recommends an action to be taken by the patient. The exit points may be customized. More specifically, the recommended action at selected exit points may be individually selected from a plurality of selectable actions. Thus, the decision flowchart may provide different recommended courses of action for a patient having the same symptoms and/or considerations based upon individual selections. The recommended action becomes an exit message for the respective exit point.

28 Claims, 6 Drawing Sheets

Example of Internal Customization Table

| Location | Provider | Time | Date | Protocol | Exit Point ID | Exit Message ID |
|---|---|---|---|---|---|---|
| Anderson Mill | Jones | 8am-5pm | ALL | Pedi earache | 3 | 3 |
| Anderson Mill | Jones | 5pm-8am | ALL | Pedi earache | 3 | 2 |

OTHER PUBLICATIONS

TeleTriage Systems™—Paper-based Protocols, printout from web site: http://www.teletriage.com/products/protocols.html, printout date: Apr. 2, 2001, original posting date: unknown, 6 pages.

Harvard Medical School Family Health Guide, A.L. Komaroff, MD, Editor in Chief, Simon Schuster, New York, NY, Copyright © 1999 by President and Fellows of Harvard College, excerpts from Symptom Charts, pp. 171-173, 336.

ZymeTx, Inc.—Physician Resources: Influenza Disease Management Program, printout from web site: http://www.zymetx.com/physician/triage.html, printout date: Apr. 2, 2001, original posting date: unknown, 2 pages.

PCT Written Opinion for PCT/US01/11000, date of mailing: Nov. 4, 2004, 4 pages.

International Preliminary Examination Report for PCT/US01/11000, date of mailing: Aug. 19, 2005, 4 pages.

* cited by examiner

Example of Internal Customization Table

| Location | Provider | Time | Date | Protocol | Exit Point ID | Exit Message ID |
|---|---|---|---|---|---|---|
| Anderson Mill | Jones | 8am-5pm | ALL | Pedi earache | 3 | 3 |
| Anderson Mill | Jones | 5pm-8am | ALL | Pedi earache | 3 | 2 |

*Fig. 3*

Privileging for Customization

|  | Date Range | Time Range | Protocol | Exit Point ID | Exit Message ID |
|---|---|---|---|---|---|
| MOM | Customizable | Customizable | Not customizable | Not customizable | Exit Messages can be customized to reflect higher priority |
| MLM (if not locked by MOM) | Customizable | Customizable | Not customizable | Not customizable | Exit Messages can be customized to reflect higher priority |
| Doctor (if not locked by MLM or MOM) | Customizable | Customizable | Not customizable | Not customizable | Exit Messages can be customized to reflect higher priority |

*Fig. 6*

PATIENT DIAGNOSIS USING TRIAGE PROTOCOLS THAT HAVE CUSTOMIZED MESSAGES AT EXIT POINTS

CROSS-REFERENCE TO RELATED APPLICATIONS

This application claims the benefit of U.S. Provisional Application No. 60/195,001 filed Apr. 5, 2000 entitled "SYSTEM AND METHOD FOR AN ONLINE INTEGRATED PROFESSIONAL SERVICE ENVIRONMENT."

BACKGROUND OF THE INVENTION

Triage is a process for sorting injured or ill people into groups based on their need for or likely benefit from immediate medical treatment. Triage is used on the battlefield, at disaster sites, and in hospital emergency rooms when limited medical resources must be allocated.

Triage protocols (sometimes referred to as "symptom charts") have been created to assist medical providers and patients in determining what medical treatment, if any, should be received given a set of medical conditions. For example, a triage protocol for dehydration in a young pediatric patient (e.g., birth-6 yrs.) may consist of a listing of symptoms and considerations that correspond with different levels of concern. If the symptom listing and considerations indicate that the patient has emergent symptoms (i.e., symptoms that demand immediate action), then the triage protocol may indicate that the patient should seek immediate treatment (e.g., 0-60 minutes). If the symptom listing and considerations indicate that the patient has urgent symptoms, then the triage protocol may indicate that the patient should seek treatment or be seen by a medical provider for further diagnosis within 1-8 hours. If the symptom listing and considerations indicate that the patient has acute symptoms, then the triage protocol may indicate that the patient should seek treatment or be seen by a medical provider for further diagnosis within 8-24 hours.

Triage protocols or symptom charts are typically arranged in chart format. However, the triage protocol may be configured to appear in a flowchart format for easier use by the medical provider or the patient. Examples of flowchart-type symptom charts for over 100 different potential medical conditions are illustrated in the Harvard Medical School Family Health Guide, published by Simon & Schuster, Copyright ©1999 by President and Fellows of Harvard College (Anthony L. Komaroff, MD, Editor in Chief).

Triage protocols are widely used by medical facilities in responding to telephone calls from patients. This service is referred to as teletriage. Teletriage is often provided by call center services staffed by specially trained registered nurses (RN's) or doctors who can provide reliable information to individuals with questions or concerns about a medical situation. A medical plan may offer teletriage as a plan benefit.

The medical industry is slowly adopting automated tools for delivering medical services to patients. U.S. Pat. No. 5,594,638 (Iliff) describes a computerized medical diagnostic and treatment advice system that operates over a telephone network. In one feature of the system, a patient uses an automated telephone system to answer a series of screening questions related to their medical condition. After the screening questions are completed, the system software determines if the patient has a serious medical condition that requires immediate intervention. If so, then the system instructs the patient to seek immediate medical attention. Otherwise, the system software branches to other paths, such as an evaluation path. The algorithm that determines if a serious medical condition exists, as well as the message that the patient receives upon such a determination, may be customized by the entity that provides the service to its patients.

The current trend in medicine is to provide Internet-based tools to improve communication between patients and medical providers, and to enable patients to become active participants in the management of their health. Flowchart-based triage protocols are an excellent resource that can be provided to patients via an electronic network, such as the Internet. However, each medical provider has specific constraints that it must impose on its patients. Thus, if flowchart-based triage protocols are to become more widely used, they must have the ability to be customized on many different levels and at a high degree of granularity. In this manner, the protocols can be tailored more specifically to the availability of medical provider resources, as well as the clinical practice patterns of the providers. Thus, the protocols can become a business tool for the medical provider, as well as a useful resource for the patient. The present invention fulfills such a need.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings an embodiment that is presently preferred. It should be understood, however, that the invention is not limited to the precise arrangements and instrumentalities shown. In the drawings:

FIG. 3 shows an internal customization table for storing settings that allow two different exit messages to be set for different time periods;

FIG. 6 shows a table of privileges available to medical providers in accordance with a preferred embodiment of the present invention.

BRIEF SUMMARY OF THE INVENTION

Figure 1:
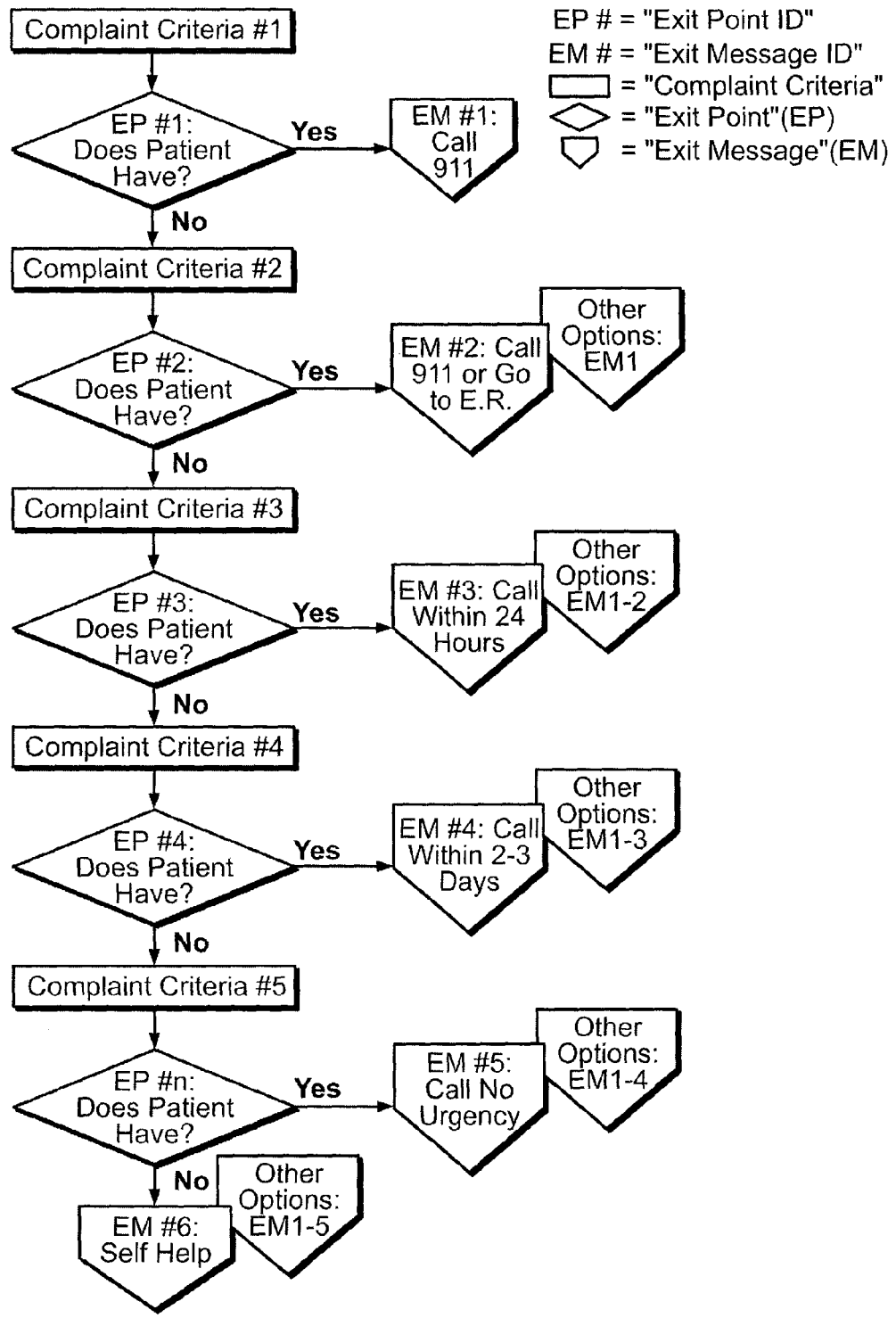
FIG. 1 shows an example of a generic flowchart of a triage protocol in accordance with the present invention.

A decision flowchart of a triage protocol is provided for a medical condition of a patient. The flowchart includes a plurality of decision blocks. Each decision block relates to one or more patient symptoms and/or considerations. A plurality of exit points are provided in the flowchart. Each exit point is associated with a respective decision block. Each exit point is reached upon the presence or absence of a symptom or consideration in the respective decision block. Each exit point recommends an action to be taken by the patient. The exit points may be customized. More specifically, the recommended action at selected exit points may be individually selected from a plurality of selectable actions. Thus, the decision flowchart may provide different recommended courses of action for a patient having the same symptoms and/or considerations based upon individual selections. The recommended action becomes an exit message for the respective exit point.

DETAILED DESCRIPTION OF THE INVENTION

Certain terminology is used herein for convenience only and is not to be taken as a limitation on the present invention.

In the drawings, the same reference letters are employed for designating the same elements throughout the several figures.

The present invention is described in the context of a software application called TalkToMeDoc that is part of a suite of applications called MyDoc Online, which is being commercialized by MyDoc Online, Inc., Round Rock, Tex. (www.mydoconline.com). However, the scope of the present invention is not limited to this particular implementation of the invention. The present invention is described in the context of a plurality of distributed computers, all of which are linked together by an electronic network A-G, such as the Internet. The computers may be any type of computing device that allows a user to interact with a web site via a web browser. For example, the computers may be a personal computers (PC) that run a Windows operating system. The computers may also be handheld, wireless devices. Patients, medical providers (e.g., hospital, clinical facility), and medical practitioners each communicate via a computer with a central host computer or a plurality of distributed host computers. The software application may be located at the host in a thin client or application service provider (ASP) architecture, or the software application may reside on the local user computers.

Definitions

The following definitions are provided to promote understanding of the invention.

Complaint criteria—discrete complaints/symptoms defined in each triage protocol.

Exit point—a logical decision point, as defined by the particular protocol, which may result in a departure from the protocol, and the display of an Exit Message.

Exit Message—directive displayed to the patient at an exit point. In one preferred embodiment of the present invention, the predefined default set of possible exit messages, in decreasing degree of severity, is:

1. Call 911
2. Go to the Emergency Room
3. Make an appointment with a physician within [4] hours *
4. Make an appointment with a physician within [3] days *
5. Make an appointment with a physician—no urgency
6. Self-help information

*items within brackets indicate a customizable parameter

Exit Message ID—unique identifier for exit messages 1,2,3,4,5,6 above.

Exit Point ID—unique identifier designating an exit point in a protocol.

Overview of Present Invention

A computer-implemented scheme provides a decision flowchart of a triage protocol for a medical condition of a patient. The flowchart includes a plurality of decision blocks. Each decision block relates to one or more patient symptoms and/or considerations. In the method, a plurality of exit points are provided in the flowchart. Each exit point is associated with a respective decision block. Each exit point is reached upon the presence or absence of a symptom or consideration in the respective decision block. Each exit point recommends an action to be taken by the patient.

An important feature of the present invention is the ability of a medical provider or medical facility to customize the exit points. More specifically, the recommended action at selected exit points may be individually selected from a plurality of selectable actions. In this manner, the decision flowchart may provide different recommended courses of action for a patient having the same symptoms and/or considerations based upon individual selections. The recommended action becomes an exit message for the respective exit point.

The decision blocks will primarily relate to patient symptoms. However, some of the decision blocks may relate to one or more patient considerations such as a demographic (e.g., age, sex) or whether the patient is currently taking certain medications.

Preferably, the patient's medical provider or medical practitioner makes the individual selections, as dictated by the privileging authorities. However, a quasi-medical administrative entity may also make the individual selections. After the selections are made, the decision flowchart may be used by patients who have been given the appropriate authorization to access the flowchart.

A plurality of different sets of exit messages can be set independently of each other. For example, if a patient's medical provider has a plurality of different medical locations, then each set of exit messages may relate to one of the medical locations. Also, if a patient's medical provider has a plurality of medical practitioners, then each set of exit messages may relate to one of the medical practitioners. Each set of exit messages may be associated with a different time period of the day or a different range of dates.

At least some of the plurality of selectable actions for each exit point include a customizable parameter. The customizable parameter is set by the medical provider or practitioner as part of the customization process. In the exit message example given above in the Definitions section, the customizable parameter is the maximum number of days that the patient should wait to make an appointment.

Each of the plurality of selectable actions for each exit point includes a default action which provides a default exit message. The default action is set in accordance with accepted medical procedures. As a safety feature, the default action may be set to have the least degree of severity of the selectable actions, thereby ensuring that selecting any of the other actions results in an exit message having a greater degree of severity than the exit message of the default action.

The individual selections may be made via a drop-down menu of a user interface, wherein each of the selectable actions is a selection in the drop-down menu. Other selection methods are within the scope of the present invention.

Preferably, the decision blocks, connector symbols, and flowline symbols of the flowchart are successively displayed to a patient in sequence and any decision blocks that occur after a patient has reached an exit point are not displayed to the patient. In this manner, the patient is not presented with additional decision blocks that may alter the patient's perceived status of his or her symptom. Also, the user interface is easier to navigate and visually interesting if the patient is only presented with decision blocks as they must be answered. Alternatively, the flowchart logic may execute in the background (not visible to the patient), and the patient may only be presented with the queries in the decision blocks, and the appropriate exit message based on the logic in the flowchart.

Each recommended action may have a corresponding reporting action that indicates whether the results of the decision flowchart are to be forwarded to a storage location for subsequent retrieval by the patient's medical provider or medical practitioner. During the customization, the reporting action is selected for each recommended action. Examples of reporting status may be: (i) send a report to a medical record; (ii) send an account of the interaction to the patient's medical practitioner; or (iii) do not report.

In an alternative embodiment of the present invention, one of the selectable actions is to branch to a subsequent decision block in the flowchart, instead of exiting the flowchart at the exit point. This option may be desirable if a particular medical provider or practitioner does not wish for the patient to exit the flowchart, even though the patient meets the condition set forth in the decision block that points to the exit point. If provided, this option should be used sparingly, because the exit points are provided to communicate an exit message to the patient, thereby terminating use of the decision flowchart.

Detailed Description

The detailed description below presumes that the patient's physician is the medical practitioner who performs the customization. However, the scope of the invention includes embodiments wherein other entities (but not including the patient) perform the customization.

The present invention provides a series of protocols that can be accessed by patients through the TalkToMeDoc module. Each protocol has the following functionality:

1. A discrete set of questions about the patient's perceived health status.
2. Answers supplied by direct input from the patient.
3. A limited form of guidance proposed to the patient based upon the patient's answers.

The physician can opt to not offer the module (in its entirety or by specific protocol) to his or her patients. If the physician offers the module, he or she will have the ability to customize certain protocol parameters determined by TalkToMeDoc.

1. Protocols
   a. Each protocol deals with a specific complaint/symptom pattern.
   b. Each protocol contains a collection of discrete Complaint Criteria.
      i. The patient indicates which symptoms/indications of the Complaint Criteria are applicable.
      ii. Based on the patient's response pattern at specified points within a given protocol, the protocol offers either an additional level of questions, or an Exit Point from the protocol with an Exit Message.
   c. Each Exit Point within each protocol offered by TalkToMeDoc contains fixed Exit Messages, some with customizable parameters. The customizable parameters are designated in brackets in the Exit Message definition above.
   d. Each Exit Point has an identifier, unique within the module ("exit point id").
   e. Each Exit Point has a default exit message assigned to it ("exit message" with "exit message id").
2. Physician Customization Capability
   a. A physician may opt to disable individual protocols. The module defaults to offer all protocols.
   b. A physician may alter the meaning of exit messages 3 and 4 by changing the values of the parameters designated in brackets in the Exit Message definition above.
   c. A physician may alter the outcome of a protocol by changing the exit message ID associated with an exit point (e.g., 3 may be changed to 4).
      i. Exit Message ID's can be changed only in a way to reflect higher acuity or urgency of patient action, never a lesser acuity relative to the default Exit Message id. This is controlled by use of dropdown box options from which the physician can select.
      ii. Changes can be made to apply by:
         1. Medical Location
         2. Physician
         3. Date range (to/from or indefinitely)
         4. Time of day (to/from: AM, PM, entire day)
   d. When a protocol customization has been designated to be active for a specifically defined time period, the protocol reverts to the TalkToMeDoc default at the end of that time period.
   e. Complaint Criteria are not subject to customization.
   f. Exit Points are not subject to customization.
3. Privileging
   a. Only a physician or physician-delegate may customize protocol elements as delineated above.
   b. All protocols default to "unlock." Locking a protocol prevents any user at a lower privileging level than the locking user to customize any element of a protocol.
      i. The Medical Organization Manager (MOM) may lock some or all of the protocols.
      ii. The Medical Location Manager (MLM) may lock some or all of the protocols in use at that location.
      iii. The hierarchy of privileging is as follows: MO ML Doctor Date Range (to/from) Time Range (to/from) protocol Exit Point ID Exit Message ID (MO=medical organization, ML=medical location)

Privileging Examples:
a. MO can lock protocol system-wide, either all specialties or specialty-specific.
b. MO can lock protocols into place at certain locations, and leave the same protocols unlocked at other locations.
c. Protocols can be "unlocked" for all physicians, enabling them to edit protocols individually.

4. Logic of the Protocol Edit Capability
   a. Physician selects from a listing of protocols.
   b. Physician is presented with columns of Complaint Criteria and the associated Exit Point and Exit Point Messages.
   c. Physician may edit the Exit Point Message ID's from a drop down box that offers only more cautious messages.
   d. Physician is then able to assign time and date ranges associated with the customized protocol.
6. Tracking and Reporting
   a. Certain features and activities within the protocol are recorded in TalkToMeDoc for documentation and auditing purposes. As described above, a reporting action may be selected for each recommended action. Examples of reporting status include:
      (i) Send a report to a medical record.
      (ii) Send an account of the interaction to the patient's medical practitioner.
      (iii) Do not report.
   b. Reports to the provider are based on privileging and patient permission.
   c. Usage tracking applies to all patient uses of the flowchart. Generic usage statistics are gathered.

In an alternative reporting scheme, the reporting status is related to the severity of the exit message. For example, if the exit message is an emergency type message, then the reporting status may be set to a default option to send an account of the interaction to the physician. If the exit message is a message instructing the patient to make an appointment with the physician, then the reporting status may be set to a default option to not send an account of the interaction to the physician. The scope of the present invention includes an alternative embodiment wherein the default options may be changed by the physician. The scope of the present invention also includes an alternative embodiment wherein the patient may selectively turn off the reporting function.

In an alternative embodiment of the present invention, the exit points are customized. One type of customization is to mark an exit point to branch to a subsequent decision block in the flowchart, instead of exiting the flowchart at the exit point. As discussed above, this option may be desirable if a particular medical provider or practitioner does not wish for the patient to exit the flowchart, even though the patient meets the condition set forth in the decision block that points to the exit point. Consider, for example, a decision block which asks the patient, "Is your skin flush?" and which has an exit point if the patient answers affirmatively. A particular physician in a particular type of practice may not believe that this condition is sufficient to warrant exiting the protocol. Accordingly, the physician may wish to mark this exit point to be skipped. This may be performed either via an additional drop-down menu item, or by providing a selection to the physician to skip the exit point. As noted above, this option should be used sparingly because the exit points are normally provided to communicate an important exit message to the patient, thereby terminating use of the decision flowchart.

FIG. 1 shows an example of a generic flowchart of a triage protocol in accordance with the present invention. The flowchart illustrates a plurality of exit points having exit point ID's (EP #1 through EP #5), and a plurality of exit messages having exit message ID's (EM #1 through EM #1 through EM #5). If the patient meets none of the complaint criteria, then the patient is provided with self-help instructions.

The flowchart may have more complex branching than the simple, linear flowchart shown in FIG. 1 as long as there are a plurality of exit points, at least some of which have customizable recommended actions (i.e., customizable exit messages). Some exit points may not be customizable. For example, a certain condition may warrant emergency treatment, and the physician may not be offered the option to change the exit message for that condition.

If the patient is presented with the decision flowchart in graphical form, the complaint criteria process symbol may provide background information to the patient to assist the patient in responding to the query presented in the subsequent decision symbol. Alternatively, if the query is short and simple, and can be fully presented within the decision symbol, then there may be no need for presenting the complaint criteria process symbol.

As discussed above, the patient may also be presented with the queries and any background information in a less graphical format, such as in a conventional questionnaire. In this embodiment, the logic of the decision flowchart determines the order of presentation of the background information and questions, and the default and customized recommended actions at the exit points determines the appropriate exit message to present to the patient.

Figure 2:
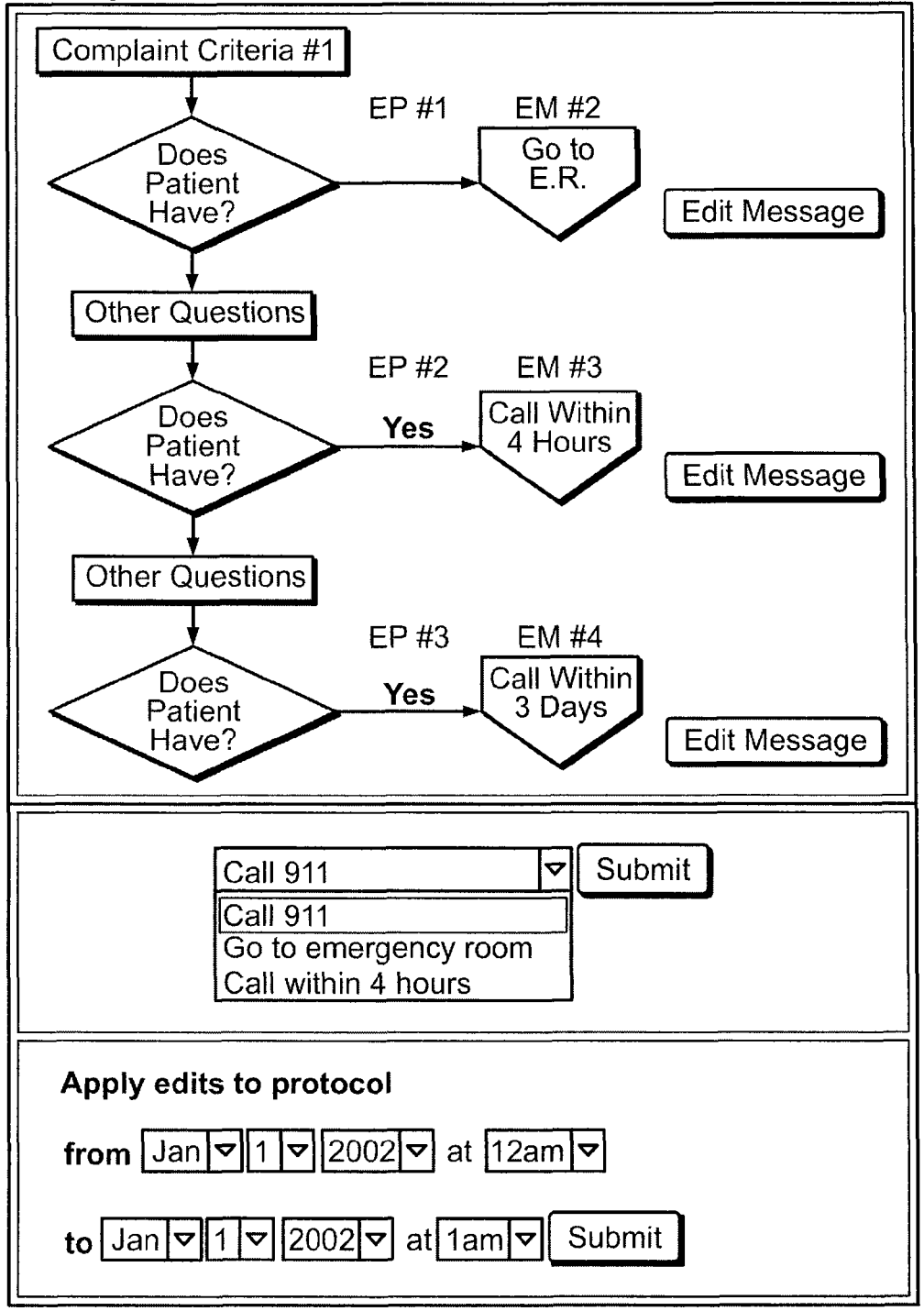
FIG. 2 shows an example of a default medical provider customization user interface in accordance with the present invention.

FIG. 2 shows an example of a default medical provider customization user interface. In this example, for each exit message, a drop-down menu appears allowing the provider to select one of three options: (1) Call 911; (2) Go to emergency room; or (3) Call within 4 hours. The provider may also choose a time frame in which the exit message is to appear, or a time frame in which the exit message is to differ from a default exit message, depending upon how the database is configured. As described above, the customization may be as granular as desired, allowing for customization based on time of day, date ranges, medical location, medical practitioner within a practice group, and the like.

As discusssed above, the default exit message may only be changed to an exit message that is more cautious than the default exit message. That is, as a safety feature, the default action is set to have the least degree of severity of the selectable actions, thereby ensuring that selecting any of the other actions results in an exit message having a greater degree of severity than the exit message of the default action. However, the scope of the present invention may include an embodiment where the default exit message may be changed to an exit message that is less or more or cautious than the default exit message (i.e., a greater or lesser degree of severity). This two-way embodiment should be made available only in limited circumstances, and to limited entities.

Figure 4:
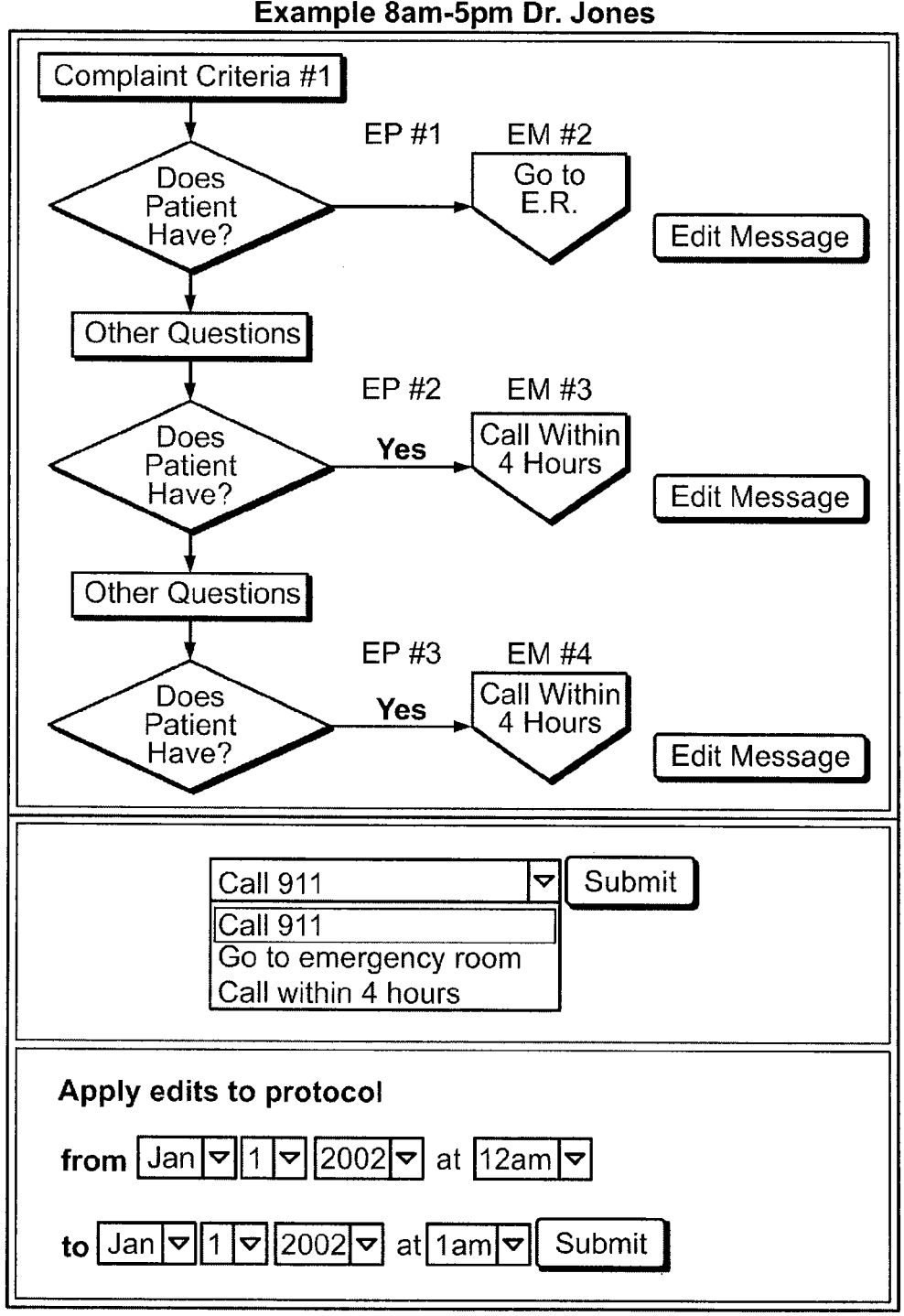
FIG. 4 shows the decision flowchart for the first time period in the table of FIG. 3.
Figure 5:
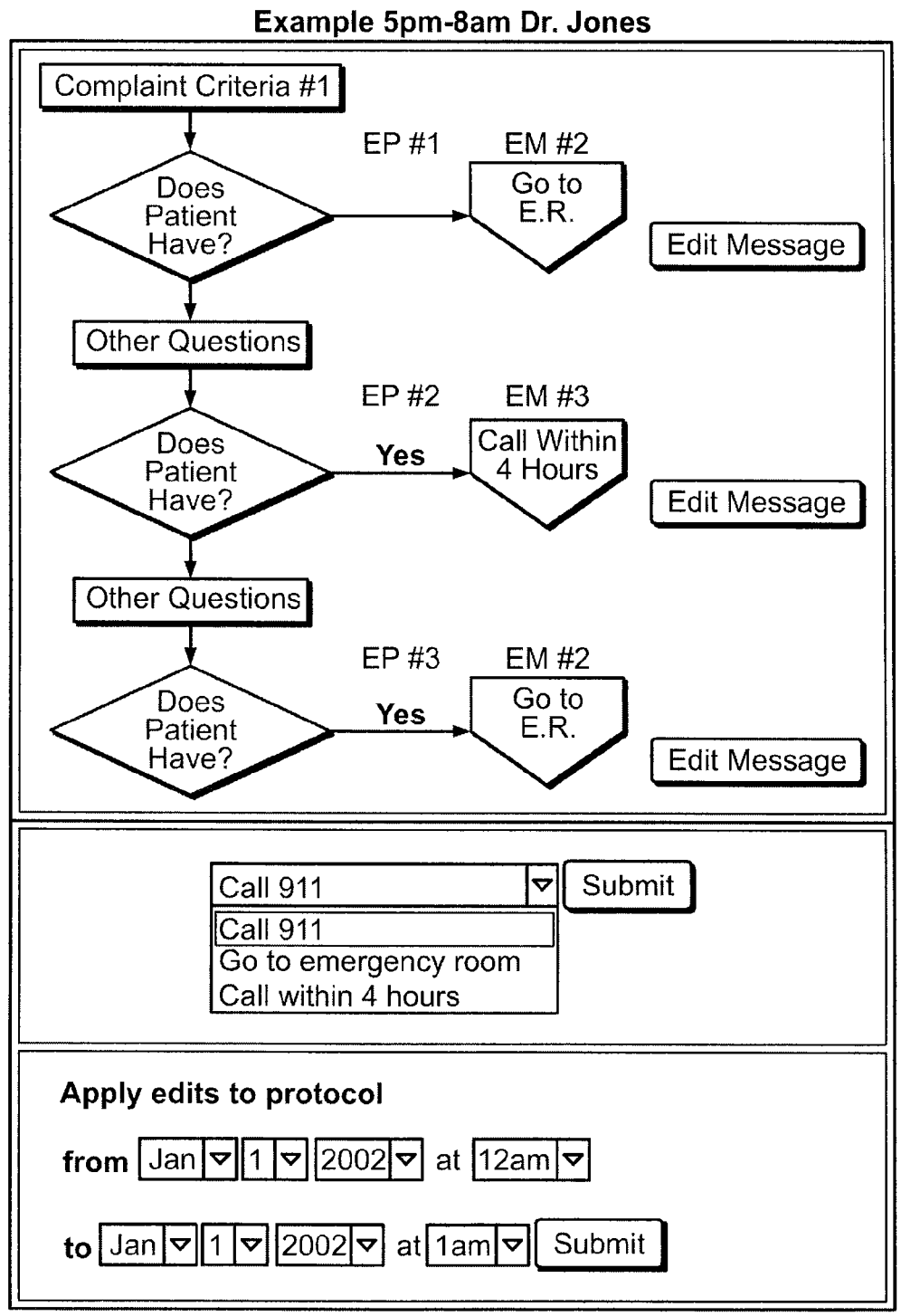
FIG. 5 shows the decision flowchart for the second time period in the table of FIG. 3.

FIGS. 3-5 show an example wherein provider, Dr. Jones, sets two different exit messages for different times of the day. FIG. 3 shows the internal customization table for storing the settings. FIG. 4 shows the decision flowchart for the first time period. FIG. 5 shows the decision flowchart for the second time period. In this example, between 8:00 am-5:00 pm, a patient who does not meet criterion 1 or 2, but who does meet criteria 3 is instructed to call the physician within four hours. However, between 5:00 pm-8:00 am, the same patient is instructed to go to the emergency room. This example may be suitable for a physician who is available for patient consultation (either in person during office hours, or by telephone) from 8:00 am-9:00 pm (four hours past 5:00 pm), but who is unavailable for patient consultation from 9:00 pm-8:00 am.

FIG. 6 shows a table of privileges for the Medical Location Manager (MLM), Medical Organization Manager (MOM), and the Doctor (medical provider), in accordance with one embodiment of the present invention.

The present invention provides important advantages over conventional patient diagnosis schemes. For example, the scheme shown in FIG. 10a of U.S. Pat. No. 5,594,638 has only one exit point (blocks 486, 488) which occurs after the patient has answered all of a set of screening questions. Individual medical providers or practitioners cannot customize the exit points in such a scheme.

The customizable exit messages of the present invention, in conjunction with the ability to control when different exit messages are provided, allows the medical provider to accommodate and control patient visit volume based on office capacity, office hours, staff and physician availability, as well as hourly, daily, weekly and seasonal peaks and valleys. For example, exit points may be set at a higher threshold (allowing for more at-home treatment) for non-urgent conditions, after hours, when a physician is unavailable for office visits. Exit points may be set at a higher threshold for a physician with a full practice, whereas exit points may be set at a lower threshold for a physician with a new practice.

Furthermore, a physician may be more likely to use prepackaged Internet-based patient management tools such as TalkToMeDoc when the physician is given the ability to customize patient care for the particular needs of his or her patients.

The present invention may be implemented with any combination of hardware and software. If implemented as a computer-implemented apparatus, the present invention is implemented using means for performing all of the steps and functions described above.

The present invention can be included in an article of manufacture (e.g., one or more computer program products) having, for instance, computer useable media. The media has embodied therein, for instance, computer readable program code means for providing and facilitating the mechanisms of the present invention. The article of manufacture can be included as part of a computer system or sold separately.

Changes can be made to the embodiments described above without departing from the broad inventive concept thereof. The present invention is thus not limited to the particular embodiments disclosed, but is intended to cover modifications within the spirit and scope of the present invention.

What is claimed is:

1. A computer-implemented method of providing a decision flowchart of a triage protocol for a medical condition of a patient, the flowchart including a plurality of decision blocks, each decision block relating to one or more patient symptoms, considerations, or symptoms and considerations, the flowchart being part of a software application, the method comprising:

(a) programming the flowchart by:
 (i) providing a plurality of exit points in the flowchart, each exit point being associated with a respective decision block, each exit point being reached upon the presence or absence of a set of symptoms, set of considerations, or set of symptoms and considerations, each exit point recommending an action to be taken by the patient;
 (ii) providing on a computer user interface that interacts with the software application a plurality of recommended actions to be taken by the patient for the same presence or absence of a set of symptoms, set of considerations, or set of symptoms and considerations, the plurality of recommended actions including recommended actions that were previously programmed into the flowchart; and
 (iii) individually selecting a recommended action via the computer user interface at selected exit points from the plurality of recommended actions, the decision flowchart thereby providing different recommended courses of action for a patient having the same presence or absence of a set of symptoms, set of considerations, or set of symptoms and considerations, the recommended action being an exit message for the respective exit point; and
(b) providing the programmed flowchart for use by a patient who has a medical condition.

2. The method of claim 1 wherein step (a) further comprises:
 (iv) providing a plurality of different sets of exit messages that can be set independently of each other.

3. The method of claim 2 wherein the patient's medical provider has a plurality of different medical locations, each set of exit messages relating to one of the medical locations.

4. The method of claim 2 wherein the patient's medical provider has a plurality of medical practitioners, each set of exit messages relating to one of the medical practitioners.

5. The method of claim 2 wherein each set of exit messages is associated with a different time period of the day or a different range of dates.

6. The method of claim 1 wherein the plurality of selectable actions for each exit point includes a default action which provides a default exit message.

7. The method of claim 6 wherein the plurality of selectable actions have different degrees of severity and the default action has the least degree of severity of the selectable actions.

8. The method of claim 1 wherein at least some of the plurality of selectable actions for each exit point includes a customizable parameter, and step (a) further comprises:
 (iv) selecting a parameter for each of the customizable parameters prior to step (a)(iii).

9. The method of claim 1 wherein the patient's medical provider makes the individual selections.

10. The method of claim 1 wherein the individual selections are made via a drop-down menu of the computer user interface, each of the selectable actions being a selection in the drop-down menu.

11. The method of claim 1 wherein a patient consideration is a patient demographic.

12. The method of claim 1 wherein the decision blocks are successively displayed in sequence and any decision blocks that occur after a patient has reached an exit point are not displayed to the patient.

13. The method of claim 1 wherein each recommended action has a corresponding reporting action that indicates whether the results of the decision flowchart are to be forwarded to a storage location for subsequent retrieval, and step (a) further comprises:
 (iv) individually selecting the reporting action for each recommended action.

14. The method of claim 1 wherein one of the selectable actions is to branch to a subsequent decision block in the flowchart, instead of exiting the flowchart at the exit point.

15. An article of manufacture for providing a decision flowchart of a triage protocol for a medical condition of a patient, the flowchart including a plurality of decision blocks, each decision block relating to one or more patient symptoms, considerations, or symptoms and considerations, the flowchart being part of a software application, the article of manufacture comprising a computer-readable medium encoded with computer-executable instructions for performing a method comprising:

(a) programming the flowchart by:
 (i) providing a plurality of exit points in the flowchart, each exit point being associated with a respective decision block, each exit point being reached upon the presence or absence of a set of symptoms, set of considerations, or set of symptoms and considerations, each exit point recommending an action to be taken by the patient;
 (ii) providing on a computer user interface that interacts with the software application a plurality of recommended actions to be taken b y the patient for the same presence or absence of a set of symptoms, set of considerations, or set of symptoms and considerations, the plurality of recommended actions including recommended actions that were previously programmed into the flowchart; and
 (iii) individually selecting a recommended action via the computer user interface at selected exit points from the plurality of recommended actions, the decision flowchart thereby providing different recommended courses of action for a patient having the same presence or absence of a set of symptoms, set of considerations, or set of symptoms and considerations, the recommended action being an exit message for the respective exit point; and
(b) providing the programmed flowchart for use by a patient who has a medical condition.

16. The article of manufacture of claim 15 wherein the computer-executable instructions of step (a) perform a method further comprising:
 (iv) providing a plurality of different sets of exit messages that can be set independently of each other.

17. The article of manufacture of claim 16 wherein the patient's medical provider has a plurality of different medical locations, each set of exit messages relating to one of the medical locations.

18. The article of manufacture of claim 16 wherein the patient's medical provider has a plurality of medical practitioners, each set of exit messages relating to one of the medical practitioners.

19. The article of manufacture of claim 16 wherein each set of exit messages is associated with a different time period of the day or a different range of dates.

20. The article of manufacture of claim 15 wherein the plurality of selectable actions for each exit point includes a default action which provides a default exit message.

21. The article of manufacture of claim 20 wherein the plurality of selectable actions have different degrees of severity and the default action has the least degree of severity of the selectable actions.

22. The article of manufacture of claim 15 wherein at least some of the plurality of selectable actions for each exit point includes a customizable parameter, the computer-executable instructions of step (a) performing a method further comprising:
   (iv) selecting a parameter for each of the customizable parameters prior to step (a)(iii).

23. The article of manufacture of claim 15 wherein the patient's medical provider makes the individual selections.

24. The article of manufacture of claim 15 wherein the individual selections are made via a drop-down menu of the computer user interface, each of the selectable actions being a selection in the drop-down menu.

25. The article of manufacture of claim 15 wherein a patient consideration is a patient demographic.

26. The article of manufacture of claim 15 wherein the decision blocks are successively displayed in sequence and any decision blocks that occur after a patient has reached an exit point are not displayed to the patient.

27. The article of manufacture of claim 15 wherein each recommended action has a corresponding reporting action that indicates whether the results of the decision flowchart are to be forwarded to a storage location for subsequent retrieval, the computer-executable instructions of step (a) performing a method further comprising:
   (iv) individually selecting the reporting action for each recommended action.

28. The article of manufacture of claim 15 wherein one of the selectable actions is to branch to a subsequent decision block in the flowchart, instead of exiting the flowchart at the exit point.

* * * * *